United States Patent
Kartoun et al.

(10) Patent No.: US 12,251,208 B2
(45) Date of Patent: Mar. 18, 2025

(54) TIME CONTROLLED MEDICATION

(71) Applicant: INTERNATIONAL BUSINESS MACHINES CORPORATION, Armonk, NY (US)

(72) Inventors: Uri Kartoun, Cambridge, MA (US); Zachary A. Silverstein, Austin, TX (US); Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1144 days.

(21) Appl. No.: 17/106,302

(22) Filed: Nov. 30, 2020

(65) Prior Publication Data
US 2022/0168551 A1 Jun. 2, 2022

(51) Int. Cl.
*A61B 5/07* (2006.01)
*A61K 9/20* (2006.01)
(Continued)

(52) U.S. Cl.
CPC .............. *A61B 5/07* (2013.01); *A61K 9/2086* (2013.01); *A61M 31/002* (2013.01); *B01J 13/04* (2013.01);
(Continued)

(58) Field of Classification Search
CPC .. A61B 5/07; A61B 2562/162; A61K 9/2086; A61M 31/002; A61M 2205/18;
(Continued)

(56) References Cited

U.S. PATENT DOCUMENTS 10,521,561 B1 * 12/2019 Euliano ................. A61B 5/065
2002/0015728 A1 2/2002 Payumo
(Continued)

OTHER PUBLICATIONS

Disclosed Anonymously, "Does Fast Dissolve Antacid Tablet, Chewable Interact with other Medications?" WebMD, https://www.webmd.com/drugs/2/drug-64322/fast-dissolve-antacid-oral/details/list-interaction-medication, Jun. 12, 2020, pp. 1-4.
(Continued)

*Primary Examiner* — David J. McCrosky
(74) *Attorney, Agent, or Firm* — Robert R. Aragona

(57) ABSTRACT

A method, a computer program product, and a computer system provide medications to a patient with a time gap. The method includes determining a dissolving pattern for the patient. The dissolving pattern includes a medication dissolving rate for a first medication prescribed to the patient and a filler dissolving rate for a filler selected so that the time gap is elapsed prior to a second medication being provided after the first medication. The medication dissolving rate and the filler dissolving rate are specific to the patient. The method includes determining dimensions of the first medication to correspond to a dosage of the prescribed first medication and dimensions of the filler to correspond to the time gap. The method includes providing a pill including at least the first medication and the filler, the first medication surrounding the filler such that the first medication is dissolved prior to the filler being dissolved.

17 Claims, 8 Drawing Sheets

(51) Int. Cl.
| | |
|---|---|
| *A61M 31/00* | (2006.01) |
| *B01J 13/04* | (2006.01) |
| *B01J 13/22* | (2006.01) |
| *G16H 20/10* | (2018.01) |
| *A61J 3/00* | (2006.01) |

(52) U.S. Cl.
CPC .............. *B01J 13/22* (2013.01); *G16H 20/10* (2018.01); *A61B 2562/162* (2013.01); *A61J 3/007* (2013.01); *A61M 2205/18* (2013.01); *A61M 2205/3553* (2013.01)

(58) Field of Classification Search
CPC .. A61M 2205/3553; B01J 13/04; B01J 13/22; G16H 20/10; G16H 70/40; G16H 10/60; A61J 3/007
See application file for complete search history.

(56) References Cited

U.S. PATENT DOCUMENTS

| | | | |
|---|---|---|---|
| 2002/0104848 A1 | 8/2002 | Burrows | |
| 2003/0198677 A1 | 10/2003 | Pryce Lewis | |
| 2004/0005360 A1 | 1/2004 | Wang | |
| 2008/0284599 A1* | 11/2008 | Zdeblick | G06K 7/10168 340/572.1 |
| 2009/0306633 A1 | 12/2009 | Trovato | |
| 2013/0310664 A1 | 11/2013 | Kozloski | |
| 2014/0326744 A1 | 11/2014 | Ratnakar | |
| 2018/0350178 A1 | 12/2018 | Poddar | |
| 2019/0016048 A1* | 1/2019 | Parietti | A61K 9/4808 |
| 2019/0198144 A1* | 6/2019 | Blackley | G16H 50/20 |
| 2019/0209468 A1 | 7/2019 | Deng | |
| 2021/0008869 A1 | 1/2021 | Rodriguez Bravo | |

OTHER PUBLICATIONS

Disclosed Anonymously, "Printing Pills: FDA Approves First 3-D Printed Drug," Harvard University Graduate School of Arts and Sciences, http://sitn.hms.harvard.edu/flash/2015/printing-pills-fda-approves-first-3-d-printed-drug/, Aug. 11, 2015, pp. 1-6.

Konta, et al., "Personalised 3D Printer Medicines: Which Techniques and Polymers Are More Successful?" Bioengineering 2017, 4, 79; doi:10.3390/bioengineering4040079, www.mdpi.com/journal/bioengineering, Sep. 22, 2017, pp. 1-16.

Mearian, "This is the First 3D-Printed Drug to Win FDA Approval," Computerworld, https://www.computerworld.com/article/3048823/this-is-the-first-3d-printed-drug-to-win-fda-approval.html, Mar. 28, 2016, pp. 1-4.

Mell et al., "The NIST Definition of Cloud Computing", National Institute of Standards and Technology, Special Publication 800-145, Sep. 2011, pp. 1-7.

Pravin, et al., "Integration of 3D printing with dosage forms: A new perspective for modern healthcare," Biomedicine & Pharmacotherapy, vol. 107, https://doi.org/10.1016/j.biopha.2018.07.167, Mar. 19, 2018, pp. 146-154.

Taheri, "Printing the Future of Medicine," Evoluted New Media, http://www.labnews.co.uk/article/2025935/printing_the_future_of_medicine, Jul. 7, 2016, pp. 1-9.

Clark, "Is it dangerous to take different medicines at the same time?", Dec. 22, 2010, https://www.netdoctor.co.uk/medicines/a4461/is-it-dangerous-to-take-dif . . . , Netdoctor, pp. 1-5.

Condie, "Edible Electronics could be providing medical treatments in five years", Sep. 22, 2015, Cosmos, The Science of Everything Newsletter, pp. 1-3.

Jain, Edible Sensor that Detects Effects of Food on body, Digestive Ailments, Dec. 12, 2017, https://www.ibtimes.com/edible-sensor-detects-effects-food-body-digesti . . . , pp. 1-8.

Medline Plus, "Taking multiple medicines safely", https://medlineplus.gov/ency/patientinstructions/000883.htm, printed Nov. 30, 2020, pp. 1-4.

MIT Technology Review, "Edible electronics tattooed on your food could help track your health", https://www.technologyreview.com/2018/02/06/145801/edible-electronic . . . , Feb. 6. 2-18, pp. 1-10.

Mukherjee, "Scientists working to develop edible electronic pills that cound be powered by our stomach acid", Hexapolis, an online digest dabbling in intriguing enterprise, Jan. 2, 2020, pp. 1-5.

UK International Search Report, Application No. GB2116124.5, Reference : DP/P49777GB, Dated Apr. 26, 2022, pp. 1-4.

Tucker Laura, "Technology Now Reaching to Food and Drugs with edible electronics", Mar. 6, 2018, pp. 1-6, https://www.maketecheasier.com/food-drugs-edible-electronics/.

* cited by examiner

SIGNAL PILL
200

MULTI-MEDICATION PILL
300

TIME CONTROLLED MEDICATION

BACKGROUND

The exemplary embodiments relate generally to medicine, and more particularly to a pill that is manufactured based on a determined dissolving pattern specific to a patient to prevent improper drug interaction.

Medicines have been developed to treat or provide relief for a variety of different illnesses or conditions. A patient may have a plurality of these illnesses and conditions. Thus, a physician may prescribe a respective medication for each of these illnesses and conditions. The medication may be ingested or introduced into the patient's body in different forms. A conventional approach is to manufacture the medication in pill or capsule form in which the patient ingests the pill at the patient's convenience based on a frequency instruction from the prescribing physician. A medication may have side effects from use that may or may not be experienced by the patient. The side effects may be determined from research efforts such as trial tests for single or multiple medications. Furthermore, a first medication may include a certain chemical that may interact with a certain chemical included in a second medication. Thus, if the patient were to ingest the first medication and the second medication with an overlap, an unexpected side effect may result. Accordingly, a patient must separate the ingestion of the first and second medications to prevent any unexpected side effect that may occur.

SUMMARY

The exemplary embodiments disclose a method, a computer program product, and a computer system for providing medications to a patient with a time gap. The method comprises determining a dissolving pattern for the patient. The dissolving pattern includes a medication dissolving rate for a first medication prescribed to the patient and a filler dissolving rate for a filler selected so that the time gap is elapsed prior to a second medication being provided after the first medication. The medication dissolving rate and the filler dissolving rate are specific to the patient. The method comprises determining dimensions of the first medication to correspond to a dosage of the prescribed first medication and dimensions of the filler to correspond to the time gap. The method comprises providing a pill including at least the first medication and the filler, the first medication surrounding the filler such that the first medication is dissolved prior to the filler being dissolved.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
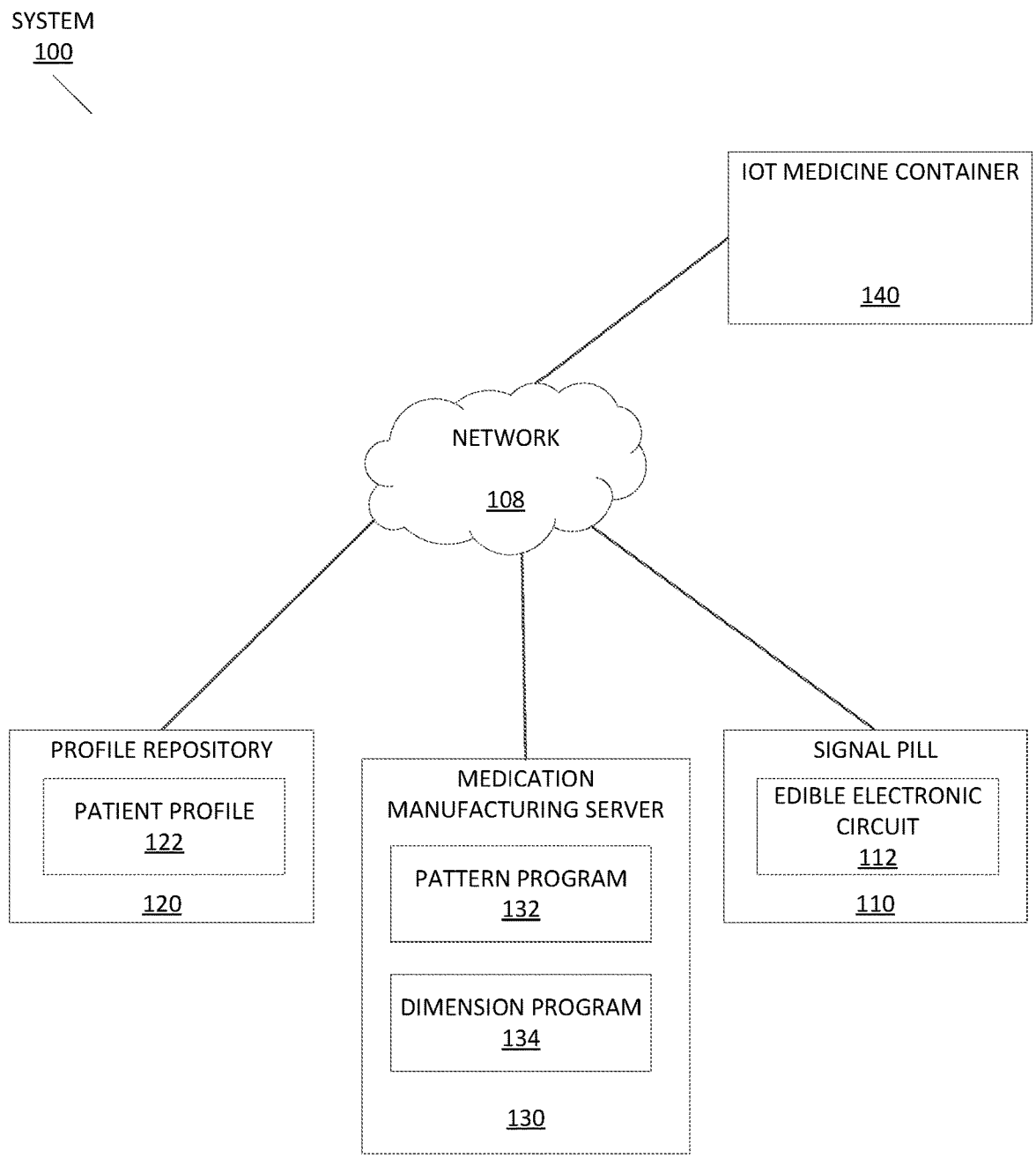
FIG. 1 depicts an exemplary schematic diagram of a medication system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

The exemplary embodiments are directed to a method, computer program product, and system for providing medications to a patient with a time gap. As will be described in further detail below, the exemplary embodiments provide the time gap between medications being taken by a patient to prevent any unexpected side effect from occurring. In providing the time gap, the exemplary embodiments determine between a multi-medication pill and a signal pill. The exemplary embodiments may determine a manner of manufacturing the multi-medication pill with a filler that creates the time gap for two different medications included in the multi-medication pill from having a drug interaction. The exemplary embodiments may determine a manner of manufacturing the signal pill with a first medication, a filler, and an edible electronic circuit where the edible electronic circuit generates a signal indicative of the time gap for a second medication to be taken to prevent a drug interaction with the first medication. Key benefits of the exemplary embodiments may include preventing any inadvertent drug interaction involving at least two medications being taken by a patient, particularly for patient error in taking a first medication and taking a second medication too early while the first medication is still present for the drug interaction to occur. Detailed implementation of the exemplary embodiments follows.

Drug interactions may occur when an individual (e.g., a patient) concurrently takes two or more different medications. In an exemplary situation, the medications may be taken for the same illness such as quinsy which is an abscess in the throat. Accordingly, the patient may need the combination of an antibiotic and a painkiller. In another exemplary situation, the patient may suffer concurrently from two distinct conditions such as high blood pressure and arthritis. Accordingly, the patient may need to take an antihypertensive and an anti-inflammatory. Medications may often affect the functionality of one another inside the patient's body. That is, consuming multiple medications may produce inadvertent effects such as increased effects, further side effects, decreased effectiveness of one or more of the medications, etc. The extent of a drug interaction may also depend on other factors that are subjective to the patient (e.g., weight, age, health condition, sensitivity to various medications, sensitivity to dosages of medication, etc.).

Conventional approaches in delivering medications to a patient involve many different considerations and preventative measures. For example, a conventional approach encapsulates a toxic core within a non-toxic region in an oral dosage of medication. This conventional approach prints a three-dimensional medication to minimize creating airborne particles of the toxic drug during manufacture. In another example, a conventional approach provides a sensor-based container for pills to reduce likelihood for poisoning. However, these conventional approaches are not directed toward a time gap separating two medications being taken by a patient.

With regard to multiple medications, additional conventional approaches provide some manner in which to provide respective medications. An ordinary approach involves the patient being responsible for taking each medication at the direction of the prescribing physician or pharmacist. However, this approach lends itself to patient error that may result in a drug interaction. In a further example, a conventional approach describes a three-dimensional printing mechanism for multi-ingredient pills, specifically for "zero-order release" profile dosages. In yet another example, a conventional approach describes a mechanism to release ingredients in a diffusion-controlled dosage form manufactured with three-dimensional printing. However, a major technical challenge for conventional approaches is to develop a mechanism capable of calculating the dimensions of the pill with the proper dosage and determining the type of material to separate each medication that may be included in a multi-medication pill. Another technical challenge is to integrate an edible sensing technology with a personalized three-dimensional pill to notify a patient of an end to a release of a first medication and an upcoming release of a second medication.

The exemplary embodiments are configured to provide a pill that allows for sufficient time to separate a release of two or more medications in order to prevent drug interaction, particularly when that drug interaction would create a negative effect. The exemplary embodiments may determine a pattern associated with medicine adsorption, dissolving of medication and other materials, etc. that may be specific to a patient for a variety of different reasons. Based on the pattern, the exemplary embodiments may manufacture the pill in different forms (e.g., a multi-medication pill or a signal pill) that create the necessary time gap in separating two or more medications that are taken by the patient.

Thus, while taking multiple medications within a short time span (e.g., for one or several diseases), the exemplary embodiments are configured to ensure that a time gap between any pair of medications is sufficiently long to reduce a likelihood for drug interaction. As different people have different absorption patterns of different types of medication and one person may have different absorption patterns for a single medicine consumed in different time frames, the exemplary embodiments may personalize the pill that is manufactured. If medications are not taken in proper time gaps, the patient may be at an increased risk for a drug interaction or the treatment may be unnecessarily delayed. In this manner, the exemplary embodiments identify medicine adsorption patterns of any patient such that the patient may be notified when the next medication may be taken or is taking effect to reduce the likelihood for a negative drug interaction.

It is noted that the description of the exemplary embodiments herein utilizes a variety of terms. However, some of these terms may be used interchangeably to substantively represent the same concept. For example, the terms "medication," "medicine," "drug," "ingredient," or the like are used interchangeably throughout the description of the exemplary embodiments.

FIG. 1 depicts a medication system 100, in accordance with the exemplary embodiments. According to the exemplary embodiments, the medication system 100 may include a signal pill 110, a profile repository 120, a medication manufacturing server 130, and an Internet of Things (IoT) medicine container 140, which may all be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted. The medication system 100 represents a communication arrangement in which the components thereof are configured to exchange data with one another in a direct or indirect manner.

As will be described below, the components of the medication system 100 may operate with only select other components. For example, the signal pill 110 and the IoT medicine container 140 may operate in a cooperative manner. In another example, the medication manufacturing server 130 may operate in a cooperative manner with the profile repository 120. However, such an arrangement is only for illustrative purposes. In view of the description of the exemplary embodiments, one skilled in the art will understand various modifications that may be made such that the components of the medication system 100 may operate cooperatively with other components that may otherwise not be operationally associated.

In the exemplary embodiments, the network 108 may be a communication channel capable of transferring data between connected devices. Accordingly, the components of the medication system 100 may represent network components or network devices interconnected via the network 108. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a Bluetooth network, a WiFi network, or a combination thereof. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices. For example, the network 108 may also represent direct or indirect wired or wireless connections between the components of the medication system 100 that do not utilize the network 108.

In the exemplary embodiments, the signal pill 110 may include an edible electronic circuit (EEC) 112 and represent any medication having a predetermined dosage that is configured to address an illness and/or condition (hereinafter referred to collectively as a "condition") of a patient. The communicative functionalities that the signal pill 110 may perform is described in greater detail as a hardware implementation with reference to FIG. 7, as part of a cloud implementation with reference to FIG. 8, and/or as utilizing functional abstraction layers for processing with reference to FIG. 9.

As will be described in further detail below, the pill that is provided to the patient for the one or more conditions of the patient may be in the form of a multi-medication pill or the signal pill 110. The signal pill 110 may include a medication portion that surrounds a filler that surrounds the EEC 112. An example of the signal pill 110 will be described in further detail below. Based on various determinations that will be described below, the medication manufacturing system 100 may be configured to determine whether the multi-medication pill may be used or whether the signal pill 110 may be preferred for a given patient.

In the exemplary embodiments, the EEC 112 may act as a client in a client-server relationship and may be a component equipped with a software, hardware, and/or firmware based application capable of measuring and exchanging time gap data via the network 108. In embodiments, the EEC 112 may perform operations upon being powered through contact with naturally produced chemicals in the patient's body such that the operations allow interaction with one or more components of the medication system 100, and utilize various wired and/or wireless connection protocols for data transmission and exchange associated with measuring a dissolving pattern specific to the patient, including Bluetooth, 2.4 gHz and 5 gHz internet, near-field communication, Z-Wave, Zigbee, etc.

The EEC 112 may be manufactured in any of a variety of manners that one skilled in the art will understand. For example, conventional approaches utilize ingestible cameras for gastrointestinal surgeries. In another example, conventional approaches use sensors attached to medications that are used to study how drugs are broken down in the body. The edible sensor may help researchers and doctors to study gastrointestinal diseases better. A digestible capsule or pill (hereinafter collectively referred to as a "pill") may easily be swallowed and subsequently dissolved in the stomach. Accordingly, conventional edible circuits may assist in detecting diseases, monitoring digestive parameters, etc. with a variety of manners in which the edible circuits are made and how the edible circuits generate power. The exemplary embodiments may be utilized and/or modified to incorporate any of the types of edible circuits with the different ways of manufacturing and powering such edible circuits.

According to an exemplary implementation, the EEC 112 may be equipped with a power source that is activated upon coming into contact with a naturally produced chemical in the patient's body. For example, the EEC 112 may be piezoelectric such that contact with stomach acids in the patient produces piezoelectricity that powers the components of the EEC 112. The EEC 112 may include circuitry components configured to perform select operations. For example, the EEC 112 may include a signal generating component that is activated upon the EEC 112 being powered. In another example, the EEC 112 may include a signal transmitting component that is also activated upon the EEC being powered. The signal that is generated by the signal generating component may subsequently be transmitted using any of the above noted transmission protocols. In a particular exemplary implementation, the transmission protocol may include a near field communication (NFC) transmission to the IoT medicine container 140. The EEC 112 may be manufactured with the same material that is conventionally used in making vitamins.

In the exemplary embodiments, the profile repository 120 may include one or more patient profiles 122 and may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of storing, receiving, and sending data to and from other computing devices. While the profile repository 120 is shown as a single device, in other embodiments, the profile repository 120 may be comprised of a cluster or plurality of electronic devices, in a modular manner, etc., working together or working independently. While the profile repository 120 is also shown as a separate component, in other embodiments, the profile repository 120 may be incorporated with one or more of the other components of the information presentation system 100. For example, the profile repository 120 may be incorporated in the medication manufacturing server 130. Thus, access to the profile repository 120 by the medication manufacturing server 130 may be performed locally. The profile repository 120 is described in greater detail as a hardware implementation with reference to FIG. 3, as part of a cloud implementation with reference to FIG. 4, and/or as utilizing functional abstraction layers for processing with reference to FIG. 5.

In the exemplary embodiments, the patient profiles 122 may each be associated with a respective patient and may be populated with various types of information that may be used for determining the type of signal pill 110 to be used and characteristics of the signal pill 110 to be provided to the patient. In an exemplary embodiment, the patient profiles 122 may include dissolving pattern information. The dissolving pattern information may be received during a monitoring phase. The monitoring phase may occur at a time prior to providing the multi-medication pill or the signal pill 110. For example, a patient may be placed on a trial run that includes a monitoring pill with an embedded circuit to capture dissolve rate. Those skilled in the art will understand how such a monitoring pill may be manufactured, particularly based on the description of the exemplary embodiments. In a particular example, the embedded circuit may be substantially similar to the EEC 112. The monitoring pill may have a medication portion surrounding the embedded circuit. Thus, during the trial run, an ingestion time may be recorded and a time when a signal from the embedded circuit is received may be recorded. A difference between these times and the physical properties of the medication portion may provide the dissolving pattern for the medication being measured. Thus, for each medication that is tested, the dissolving pattern may include medication dissolving rates for various types of medications in a selected composition (e.g., materials used for the medication, physical characteristics such as density, dimensions of the monitoring pill and the medication portion of the monitoring pill, etc.). In another example, the dissolving pattern may indicate a filler dissolving rate at which a filler is dissolved by the specific patient. In a substantially similar manner, a further monitoring pill may include an embedded circuit that is surrounded by the filler. Thus, for each filler that is tested, a time and the physical properties of the filler may provide the dissolving pattern for the filler.

The patient profiles 122 may include other information. For example, the patient profiles 122 may be populated with information recorded in electronic health records (EHRs). In another example, the patient profiles 122 may be populated with standard information that is medically or non-medically relevant to the patient (e.g., demographic information, height, weight, allergies, sensitivities, etc.). As those skilled in the art will appreciate, this type of information may be applicable in determining the dissolving rates (e.g., explaining why a dissolving rate is observed) as well as medications that may or may not be prescribed.

The IoT medicine container 140 may represent any vessel configured to store the medications that are to be taken by the patient. The IoT medicine container 140 may include a plurality of sections that may each be filled with the appropriate medications that are to be taken on a given day, at a given time during the day, etc. The IoT medicine container 140 may be equipped with locking components that lock the IoT medicine container 140 or selectively lock the sections. The IoT medicine container 140 may also include electronic components. For example, the IoT medicine container 140 may include a processor (e.g., a simple processor executing simple operations) that control various components of the IoT medicine container 140, generate signals, etc. In a particular example, the locking components may be controlled by the processor. In another example, the IoT medicine container 140 may include a signal receiving component. The signal receiving component may be configured to receive a signal from the EEC 112. In receiving the signal from the EEC 112, the processor may execute an operation that unlocks the IoT medicine container 140 or a section thereof. In a further example, the IoT medicine container 140 may include a sensor that measures sensory information with regard to the IoT medicine container 140 or a section thereof is accessed (e.g., opened and closed) as well as whether items in the IoT medicine container 140 or a section thereof have been removed. In yet another example, the IoT medicine container 140 may include an alert component that provides a sensory alarm to the patient. The processor may have a scheduling operation and a clock to trigger the alert component such that the patient is aware when a medication is to be taken. The processor may also determine when to trigger the alert component as a result of receiving the signal from the EEC 112 such that a further medication is taken with a sufficient time gap. The alert component may be a visual alarm (e.g., LED is intermittently or steadily lit), an auditory alarm (e.g., a sound may be played out until the medicine is taken), a haptic alarm (e.g., the IoT medicine container 140 may vibrate), or a combination thereof.

According to an exemplary implementation, the signal pill 110 may utilize NFC signals with the IoT medicine container 140. Accordingly, a direct communication pathway may be established between these components. However, the use of this arrangement is only illustrative. In another exemplary implementation, the patient may have a smart device that is present. The smart device may be in communicative range to establish a communication pathway with the signal pill 110 and the IoT medicine container 140. In this manner, the smart device may include an application that exchanges the signals between these components of the medication system 100. The application on the smart device may also provide a user interface. Accordingly, the alert component may alternatively or additionally be configured on the smart device. The application on the smart device may also replace operations described above for the IoT medicine container 140. For example, the smart device may include the scheduling application and the clock. In this manner, the IoT medicine container 140 may be designed with less complexity and utilize processing capabilities of the smart device.

In the exemplary embodiments, the medication manufacturing server 130 may include a pattern program 132 and a dimension program 134. The medication manufacturing server 130 may be an enterprise server, a laptop computer, a notebook, a tablet computer, a netbook computer, a PC, a desktop computer, a server, a PDA, a rotary phone, a touchtone phone, a smart phone, a mobile phone, a virtual device, a thin client, an IoT device, or any other electronic device or computing system capable of receiving and sending data to and from other computing devices. While the medication manufacturing server 130 is shown as a single device, in other embodiments, the medication manufacturing server 130 may be comprised of a cluster or plurality of computing devices, working together or working independently. While the medication manufacturing server 130 is also shown as a separate component, in other embodiments, the operations and features of the medication manufacturing server 130 may be incorporated with one or more of the other components of the medication system 100. The medication manufacturing server 130 is described in greater detail as a hardware implementation with reference to FIG. 7, as part of a cloud implementation with reference to FIG. 8, and/or as utilizing functional abstraction layers for processing with reference to FIG. 9.

The medication manufacturing server 130 may provide operations involved in manufacturing the signal pill 110 and/or the multi-medication pill. For example, as described above, the patient may be in a trial run to determine medicating parameters including the type of pill to be prescribed (e.g., between the signal pill 110 and the multi-medication pill), dimensions of the pill, selections of components of the pill, etc. Accordingly, the medication manufacturing server 130 may provide a plurality of operations that may be performed prior to prescribing the pill to the patient. The medication manufacturing server 130 may also perform its operations at other intervals, particularly when the patient exhibits different dissolving patterns. In this manner, the pill that is prescribed to the patient may remain to provide a proper time gap to prevent drug interaction.

In the exemplary embodiments, the pattern program 132 may be a software, hardware, and/or firmware application configured to determine a dissolving pattern associated with a patient. Accordingly, the pattern program 132 may be utilized during a monitoring phase (e.g., the trial run) in which metabolic characteristics of the patient are determined. Specifically, the pattern program 132 may determine a rate in which chemicals that are ingested are dissolved by the patient. The chemicals may include various types of medications and various types of fillers (e.g., non-medical fillers).

As noted above, during the monitoring phase, the patient may be instructed to ingest a monitoring pill. The monitoring pill may include an embedded circuit that is substantially similar to the EEC 112. In a first type of the monitoring pill, the embedded circuit may be surrounded by a medication that is prescribed to the patient. The time that the patient ingests the monitoring pill may be recorded. At a subsequent time, the embedded circuit may become powered when the medication portion of the monitoring pill has been dissolved. As a result of being powered, the embedded circuit may transmit a signal. The time that the signal is received may also be recorded. Based on the duration of time between ingestion to the signal being received may establish the time required by the patient to dissolve the medication. The pattern program 132 may therefore establish the dissolving rate for the medication. This process may be repeated for each type of medication that is prescribed to the patient. In a second type of monitoring pill, the embedded circuit may be surrounded by a filler. The time when this monitoring pill is ingested and the time when the signal is received may also be recorded to determine the duration of time required by the patient to dissolve the filler. The pattern program 132 may therefore establish the dissolving rate for the filler. This process may be repeated for each type of filler that may be used for the pill manufactured according to the exemplary embodiments. Through this trial run, the pattern program 132 may determine the dissolving pattern for the patient.

Also noted above, this process performed by the pattern program 132 may be performed at various times. For example, this process may be performed at an initial time to establish an initial dissolving pattern for the patient. In another example, as the patient may alter the dissolving pattern, this process may be performed at a subsequent time relative to the initial time to establish a current dissolving pattern for the patient. The subsequent time may be, for example, at predetermined time intervals (e.g., after a duration of time that the pill has been taken by the patient), upon an event being determined (e.g., determining a drug interaction being present, determining a new prescription for a medication or a new filler to be used), etc. For each time that the process is performed, the dissolving pattern may be stored in the patient profile 122 for the patient.

In the exemplary embodiments, the dimension program 134 may be a software, hardware, and/or firmware application configured to determine dimensions of the pill to be prescribed to the patient. The dimension program 134 may determine the dimensions of the pill as a whole as well as the dimensions of the components of the pill.

In one manner of determining dimensions, the dimension program 134 may receive prescription information for medications that are prescribed to the patient. The prescription information may include, for example, a dosage or an amount of the medication that is to be ingested by the patient at the prescribed frequency for the medication. Based on available concentrations of the medication, the dimension program 134 may determine a volume of the medication to be included in a given pill for a given concentration.

In another manner of determining dimensions, the dimension program 134 may receive filler information for fillers to be included in the pill for the patient. Based on the filler dissolving rate for a given filler, the dimension program 134 may determine an amount of time that will elapse from using a selected amount of the filler. The amount of time that will elapse may correspond to the time gap between a first medication that is taken and a second medication that is to be taken. Thus, the dimension program 134 may determine a volume of the filler to be included in a given pill for the time gap to be accomplished where the time gap is indicative of a minimum amount of time that prevents or minimizes a drug interaction between the first and second medications.

In a further manner of determining dimension, the dimension program 134 may receive information of the EEC 112 that may be included in the pill for the patient. The EEC 112 may be manufactured with known dimensions such that all necessary components may be included. The dimensions of the EEC 112 may be set to a standard size (e.g., industry size).

Based on the volumes for the medications, the filler, and the EEC 112, the dimension program 134 may determine a minimum volume that the pill to be prescribed to the patient will occupy. For example, as a multi-medication pill, the dimension program 134 may determine a volume of an inner medication portion, a volume of the filler surrounding the inner medication portion, and a volume of an outer medication portion surrounding the filler. The dimension program 134 may thereby determine a total volume for the multi-medication pill. Based on the total volume for the multi-medication pill, the dimension program 134 may determine whether the multi-medication pill occupies an acceptable volume. For example, each patient may have a maximum pill size that may be prescribed. The maximum pill size may be determined based on various factors. In an exemplary embodiment, during the trial run, the patient may be provided various size pills. The patient may indicate a maximum size pill that the patient is able to comfortably ingest. In another example, crowd sourced information may be used to determine a maximum pill size that may be prescribed for patients matching a particular patient characteristic profile (e.g., age, patient size, etc.). The maximum pill size may define a size threshold for the patient. Thus, when the total volume of the multi-medication pill is within the size threshold (i.e., the maximum pill size), the dimension program 134 may determine that the multi-medication pill may be manufactured according to the determined dimensions and prescribed to the patient. In contrast, when the total volume of the multi-medication pill exceeds the size threshold, the dimension program 134 may determine that the multi-medication pill may have an unacceptable size. Accordingly, the dimension program 134 may determine that the signal pill 110 may be manufactured and prescribed to the patient. The dimension program 134 may determine the dimensions of the signal pill 110 in a substantially similar manner as described above with the volume of the medication, the volume of the filler, and the volume of the EEC 112 being utilized to determine the overall volume of the signal pill 110.

Figure 2:
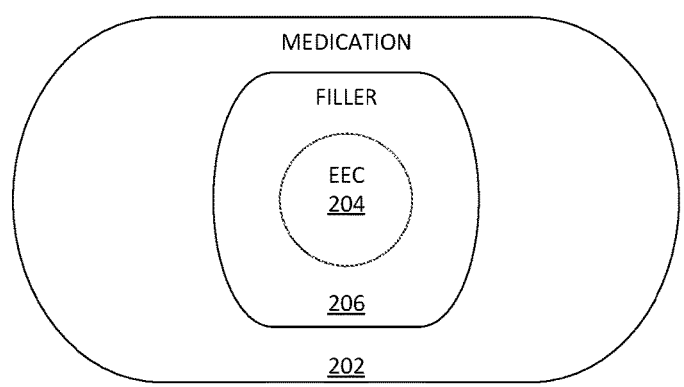
FIG. 2 depicts an exemplary signal pill 200, in accordance with the exemplary embodiments.

FIG. 2 depicts an exemplary signal pill 200, in accordance with the exemplary embodiments. The signal pill 200 may correspond to the signal pill 110 described above in reference to the medication system 100 of FIG. 1. The signal pill 200 may include a medication portion 202, an EEC portion 204, and a filler portion 206. The EEC portion 204 may correspond to the EEC 112 described above in reference to the medication system 100 of FIG. 1. As illustrated, the signal pill 200 may be arranged with the EEC portion 204 as a central portion, the filler portion 206 surrounding the EEC portion 204, and the medication portion 202 surrounding the filler portion 206. The medication portion 202 may include a first medication at the proper dosage. The filler portion 206 may include a filler at a proper volume to create a time gap. Specifically, upon ingesting the signal pill 200, the stomach acids may digest the signal pill 200 such that the medication portion 202 may dissolve. Upon the medication portion 202 dissolving, the patient may receive the first medication. When the medication portion 202 has been dissolved, the stomach acids may digest the filler portion 206. Based on the dissolving pattern of the patient, the volume of the medication portion 202 and the volume of the filler portion 206 may be set such that the medication portion 202 and the filler portion 206 being dissolved creates the time gap. Upon the filler portion 206 being dissolved after the time gap, the EEC portion 204 may be exposed to the patient's stomach acids. With the EEC portion 204 being piezoelectric, the EEC portion 204 may be powered such that a signal is generated and transmitted. The signal may be received by the IoT medicine container 140 and/or a smart device of the patient. The signal may trigger an alert for a second medication to be ingested. Since the time gap has elapsed, the patient may ingest the second medication with minimal or no drug interaction.

Figure 3:
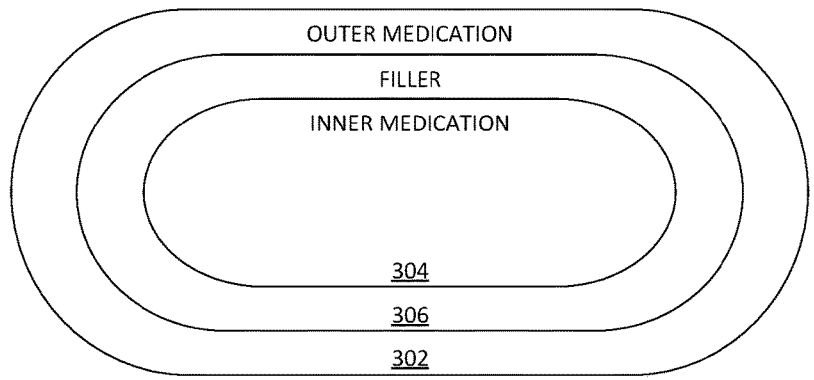
FIG. 3 depicts an exemplary multi-medication pill 300, in accordance with the exemplary embodiments.

FIG. 3 depicts an exemplary multi-medication pill 300, in accordance with the exemplary embodiments. The multi-medication pill 300 may be manufactured as a result of determining the dissolving pattern of the patient such that the overall dimensions and the constituent dimensions correspond to the proper dosages of the medications with a sufficient time gap. The multi-medication pill 300 may include an outer medication portion 302, an inner medication portion 304, and a filler portion 306. As illustrated, the multi-medication pill 300 may be arranged with the inner medication portion 304 as a central portion, the filler portion 306 surrounding the inner medication portion 304, and the outer medication portion 302 surrounding the filler portion 306. The outer medication portion 302 may include a first medication at the proper dosage. The filler portion 306 may include a filler at a proper volume to create a time gap. Specifically, upon ingesting the multi-medication pill 300, the stomach acids may digest the multi-medication pill 300 such that the outer medication portion 302 may dissolve. Upon the outer medication portion 302 dissolving, the patient may receive the first medication. When the outer medication portion 302 has been dissolved, the stomach acids may digest the filler portion 306. Based on the dissolving pattern of the patient, the volume of the outer medication portion 302 and the volume of the filler portion 306 may be set such that the outer medication portion 302 and the filler portion 306 being dissolved creates the time gap. Upon the filler portion 306 being dissolved after the time gap, the inner medication portion 304 may begin to dissolve. Upon the inner medication portion 304 dissolving, the patient may receive the second medication. Since the time gap has elapsed, the patient may receive the second medication with minimal or no drug interaction.

The above description for the multi-medication pill 300 relates to including two medications in a single pill. However, the use of only two medications is only exemplary. For example, the patient may be prescribed first, second, and third medications. According to a first exemplary scenario, the first medication may be known to have no drug interaction with the second or the third medication. However, the second medication may be known to have a drug interaction with the third medication. Thus, the multi-medication pill 300 may be manufactured such that the outer medication portion 302 may include, for example, only the second medication while the inner medication portion 304 may include the third medication, or vice versa. Due to the first medication not having any drug interaction, the first medication may be incorporated in the outer medication portion 302 or the inner medication portion 304. In this manner, for this exemplary scenario, one of the outer medication portion 302 or the inner medication portion 304 may include more than one medication. According to a second exemplary scenario, each of the first, second, and third medications may be known to have a drug interaction with the other two of the first, second, and third medications. Thus, the multi-medication pill 300 may be manufactured such that there is an additional layer. For example, the multi-medication pill 300 may include the outer medication portion 302 (e.g., which may include one of the first, second, or third medications), the filler portion 306, the inner medication portion 304 (e.g., which may include one of the remaining medications), a further filler portion (not shown), and a further inner medication portion (not shown) (e.g., which may include the last remaining medication). The filler portion 306 and the further filler portion may be sized such that a sufficient time gap is created between the outer medication portion 302 and the inner medication portion 304 and between the inner medication portion 304 and the further inner medication portion, respectively. Furthermore, additional medications may be incorporated in the various portions. Specifically, when one of the additional medications is determined to not have a drug interaction with a particular one of the medications that are to be included in the various portions, the additional medication may be incorporated with that non-reactive medication. As one skilled in the art will recognize, the multi-medication pill 300 may include any number of medication portions with filler portions disposed therebetween.

Figure 4:
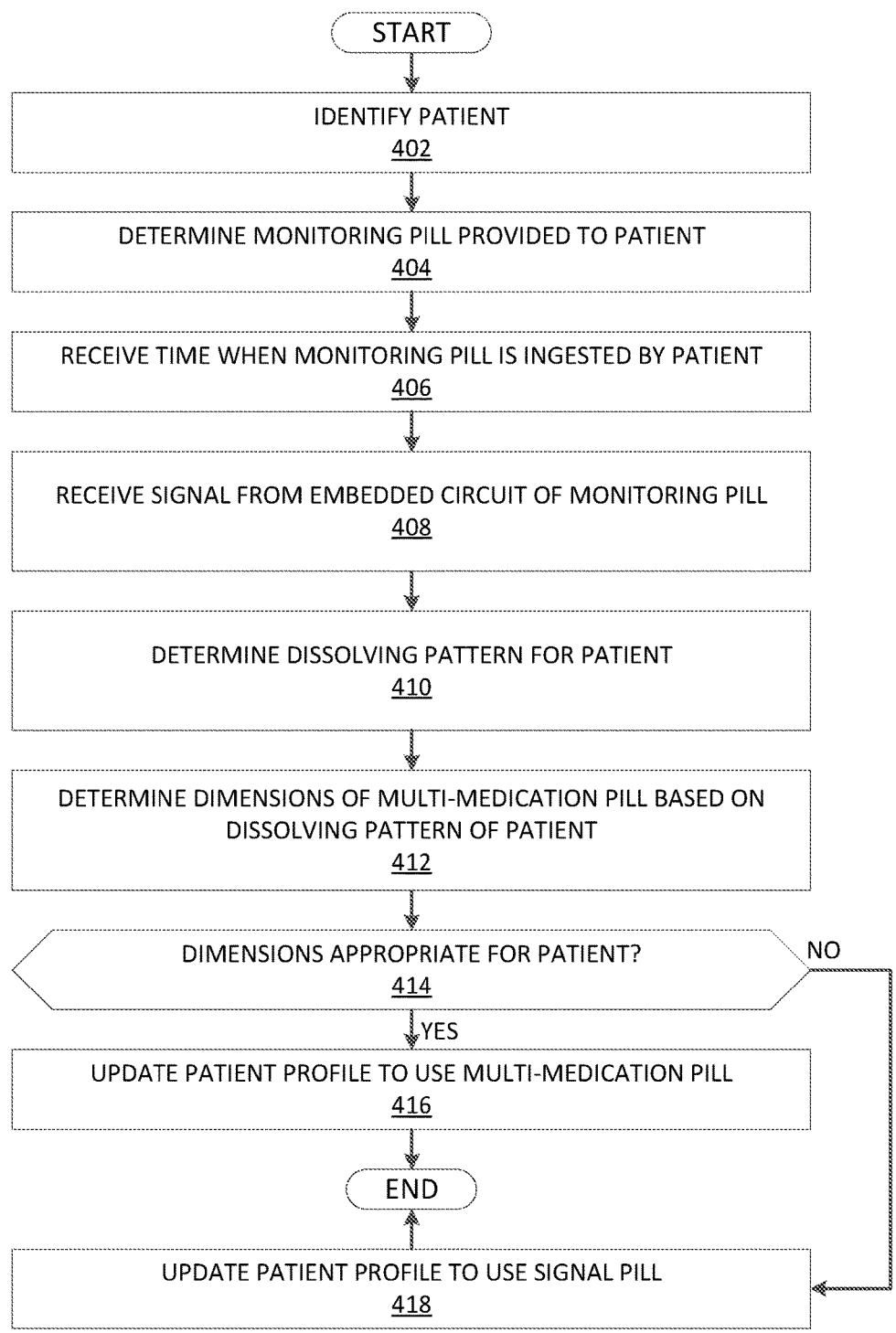
FIG. 4 depicts an exemplary flowchart of a method 400 illustrating the operations of a pattern program 132 of the medication manufacturing server 130 of the medication system 100 in determining a type of pill for a patient, in accordance with the exemplary embodiments.

FIG. 4 depicts an exemplary flowchart of a method 400 illustrating the operations of a pattern program 132 and the dimension program 134 of the medication manufacturing server 130 of the medication system 100 in determining a type of pill for a patient, in accordance with the exemplary embodiments. The method 400 may relate to a trial run performed for a patient to determine a type of pill to prescribe to the patient. Accordingly, the method 400 will be described from the perspective of the medication manufacturing server 130.

The medication manufacturing server 130 identifies the patient (step 402). During the trial run, the patient may be registered such that the patient profile 122 may be created or retrieved. For example, when the patient is a new patient for which a dissolving pattern is to be determined, the medication manufacturing server 130 may create a new patient profile 122. In another example, when the patient is to update the dissolving pattern for any of a variety of reasons (e.g., scheduled update, event triggering, etc.), the medication manufacturing server 130 may retrieve an existing patient profile 122 for the patient.

The medication manufacturing server 130 determines the monitoring pill that is provided to the patient (step 404). In an exemplary monitoring pill, the monitoring pill may include a medication that surrounds an embedded circuit where the embedded circuit may be substantially similar to the EEC 112. In another exemplary monitoring pill, the monitoring pill may include a filler that surrounds an embedded circuit.

The medication manufacturing server 130 receives a time when the monitoring pill is ingested by the patient (step 406). When the patient ingests the monitoring pill, a time may be recorded. Although there may be a slight deviation from when the monitoring pill actually starts to be dissolved, the deviation may be minimal in terms of a total time taken for the monitoring pill to be dissolved to expose the inner embedded circuit. The medication manufacturing server 130 receives a signal from the embedded circuit of the monitoring pill (step 408). As the monitoring pill begins to dissolve, a timer may track a duration taken for the medication portion or the filler portion to be dissolved to expose the embedded circuit. Once the embedded circuit is exposed to the stomach acids of the patient, the embedded circuit may be powered to trigger generation and transmission of the signal. The medication manufacturing server 130 determines a dissolving pattern of the patient (step 410). Based on the duration taken for the monitoring pill to be dissolved, the medication manufacturing server 130 may determine a dissolving rate for the patient in dissolving a selected medication or a selected filler.

The medication manufacturing server 130 determines dimensions of a multi-medication pill 300 based on the dissolving pattern of the patient (step 412). Based on the dissolving pattern and in selecting at least two medications that are prescribed for the patient, the medication manufacturing server 130 may determine constituent dimensions for an outer medication portion 302, an inner medication portion 304, and a filler portion 306. As will be described in further detail with regard to FIG. 5, the medication manufacturing server 130 may determine the dimensions utilizing various factors.

The medication manufacturing server 130 determines whether the overall dimensions of the multi-medication pill 300 is appropriate for the patient (decision 414). As described above, the patient may have a maximum pill size that may be acceptable for prescription. As a result of the multi-medication pill 300 having overall dimensions that are appropriate for the patient such as being within the size threshold defined by the maximum pill size (decision 414, "YES" branch), the medication manufacturing server 130 updates the patient profile 122 corresponding to the patient indicating that the multi-medication pill 300 is to be used (step 416). In updating the patient profile 122, the medication manufacturing server 130 may include the determined dimensions of the various portions in the multi-medication pill 300. As a result of the multi-medication pill 300 having overall dimensions that are inappropriate for the patient such as being outside the size threshold defined by the maximum pill size (decision 414, "NO" branch), the medication manufacturing server 130 updates the patient profile 122 corresponding to the patient indicating that the signal pill 200 is to be used (step 418).

Figure 5:
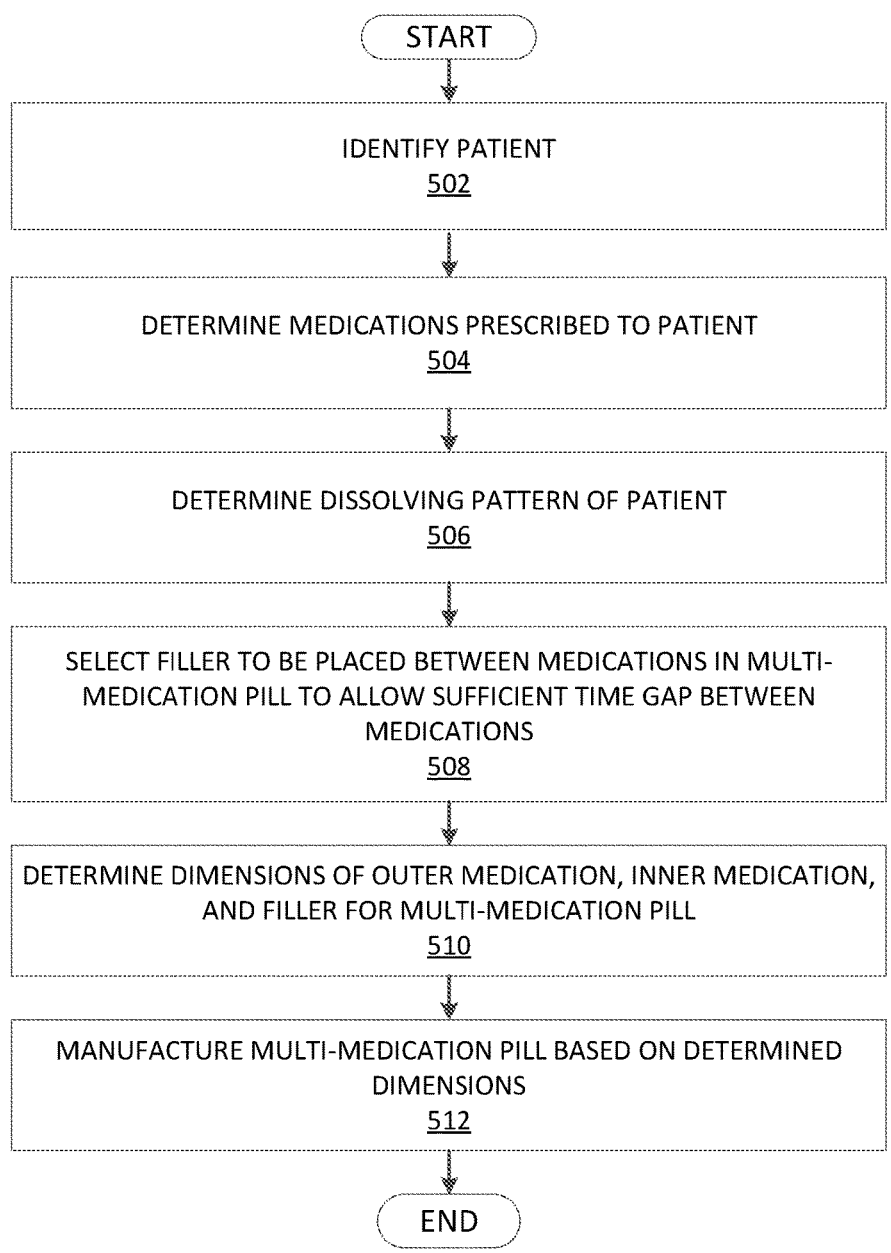
FIG. 5 depicts an exemplary flowchart of a method 500 illustrating the operations of a dimension program 134 of the medication manufacturing server 130 of the medication system 100 in determining dimensions of a multi-medication pill for a patient, in accordance with the exemplary embodiments.

FIG. 5 depicts an exemplary flowchart of a method 500 illustrating the operations of a dimension program 134 of the medication manufacturing server 130 of the medication system 100 in determining dimensions of a multi-medication pill for a patient, in accordance with the exemplary embodiments. The method 500 may relate to a trial run performed for a patient to determine acceptable dimensions of the multi-medication pill that may be prescribed to the patient. The method 500 provides further details regarding an operation of the method 400 (e.g., step 412). Accordingly, the method 500 will be described from the perspective of the medication manufacturing server 130.

The medication manufacturing server 130 identifies the patient (step 502). The medication manufacturing server 130 may identify the patient in a substantially similar manner as described above with regard to the method 400. The medication manufacturing server 130 determines medications prescribed to the patient (step 504). The patient profile 122 may include various types of information such as that recorded in an EHR. The EHR may include prescriptions for the patient that a prescribing physician may have selected. During the trial run, each of the medications corresponding to the prescriptions may have been tested to determine a respective medication dissolving rate that is stored in the patient profile 122. In addition, during the trial run, one or more fillers may have been tested to determine a respective filler rate that is stored in the patient profile 122. The medication manufacturing server 130 determines the dissolving pattern of the patient (step 506). Specifically, the dissolving pattern may reflect the various medication dissolving rates and the filler dissolving rates.

The medication manufacturing server 130 selects a filler to be placed between the medications in a multi-medication pill 300 to allow for a sufficient time gap between the medications (step 508). For example, the multi-medication pill 300 may be manufactured with a preselected filler. Accordingly, this preselected filler may be selected. In another example, the multi-medication pill 300 may be manufactured with one of a plurality of fillers. The medication manufacturing server 130 may perform various measurements and calculations with regard to each of the available fillers where each of the available fillers have been tested to have a corresponding filler dissolving rate.

The medication manufacturing server 130 determines dimensions of the outer medication portion 302, the inner medication portion 304, and the filler portion 306 for the multi-medication pill 300 (step 510). The dimensions of the outer medication portion 302 and the inner medication portion 304 may relate to a total volume of the respective medication to be included in the outer medication portion 302 such that a proper dosage is provided to the patient. Depending on a selected shape of the multi-medication pill (e.g., a standard cylindrical pill with hemi-spherical ends may be selected), the medication manufacturing server 130 may determine the dimensions of the inner medication portion 304 to exhibit the selected shape with the determined volume. The medication manufacturing server 130 may also determine the dimensions of the selected filler to exhibit the selected shape and surround the inner medication portion 304 with the determined volume for the time gap to be provided. The medication manufacturing server 130 may further determine the dimensions of the outer medication portion 306 to exhibit the selected shape and surround the filler portion 306 with the determined volume. In this manner the individual dimensions and the overall dimensions of the multi-medication pill 300 may be determined such that the medication manufacturing server 130 may provide instructions (e.g., to a pill manufacturing entity) to manufacture the multi-medication pill 300 based on the determined dimensions (step 512).

Figure 6:
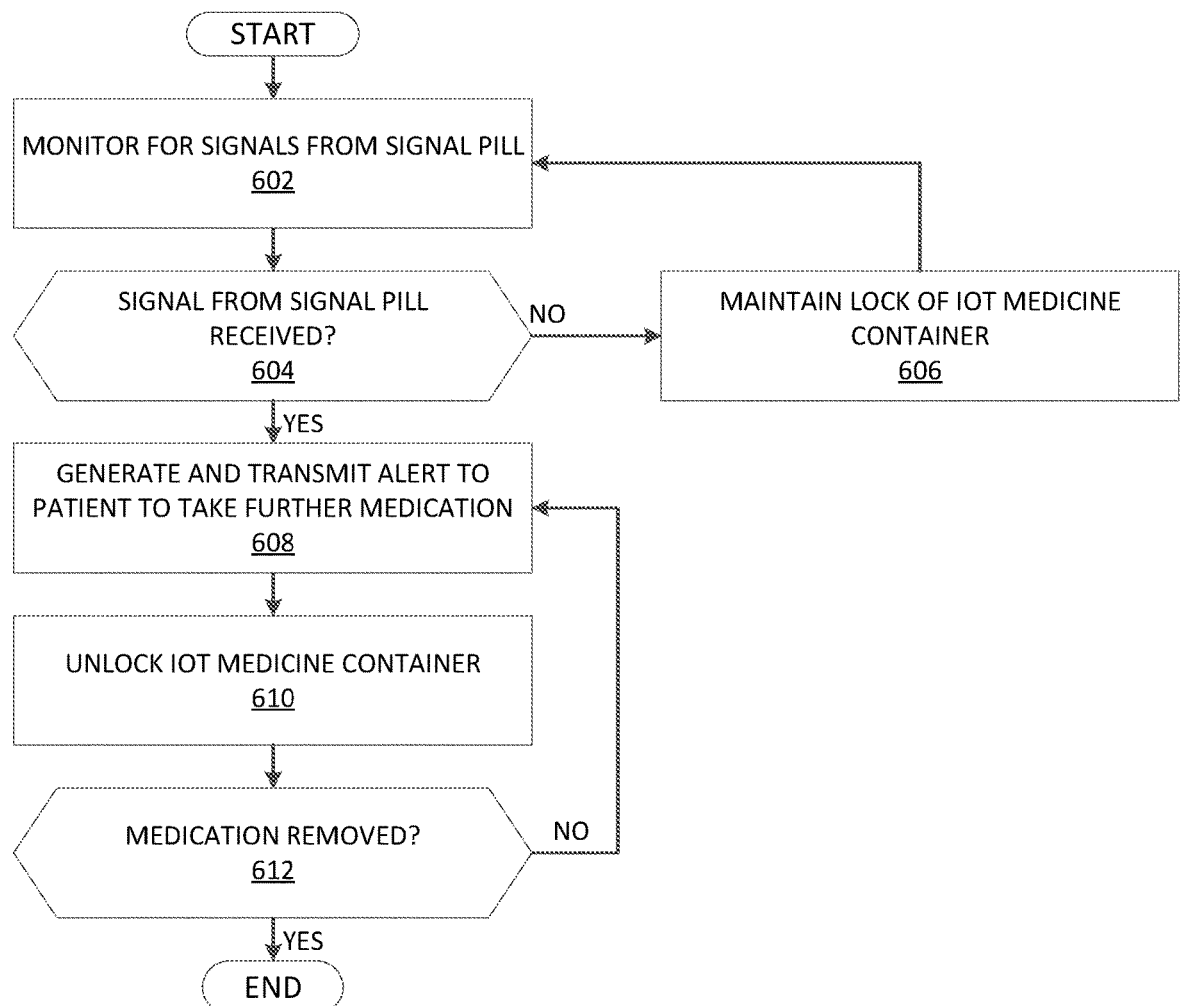
FIG. 6 depicts an exemplary flowchart of a method 600 illustrating operations of the signal pill 110 of the medication system 100 in alerting a patient to take a further dose of medication, in accordance with the exemplary embodiments.

FIG. 6 depicts an exemplary flowchart of a method 600 illustrating operations of the IoT medicine container 140 of the medication system 100 in alerting a patient to take a further dose of medication, in accordance with the exemplary embodiments. The method 600 may relate to a period of time after the trial run has been performed for a patient and the signal pill 110 has been determined as the type of pill to be prescribed to the patient. Accordingly, the method 600 will be described from the perspective of the IoT medicine container 140 that may be holding a plurality of pills that the patient may be taking. The method 600 will also be described with regard to the exemplary implementation where the signal pill 110 and the IoT medicine container 140 utilize a direct communication pathway (e.g., there is no smart device that is utilized in the method 600). However, one skilled in the art will readily understand modifications to the method 600 when a smart device is incorporated in the process.

The IoT medicine container 140 monitors for signals from the signal pill 200 (step 602). As described above, the patient may be prescribed the signal pill 200 that includes a first medication in a medication portion 202 surrounding a filler portion 206 surrounding the EEC portion 204. For example, for a particular patient, the multi-medication pill 300 may have overall dimensions where the size threshold for the patient is not satisfied. Accordingly, the signal pill 200 may be manufactured and provided to the patient. The patient may have ingested the signal pill 200 at a designated time as prescribed by the prescribing physician or pharmacist. Once ingested, the signal pill 200 may begin to dissolve due to the stomach acids of the patient. Once the medication portion 202 dissolves, the filler portion 206 may begin to dissolve. Once the filler portion 206 has dissolved and the time gap for the medications prescribed to the patient has elapsed, the EEC 112 in the EEC portion 204 may be powered and activated. The EEC 112 may therefore start to generate and transmit/broadcast a signal.

The IoT medicine container 140 determines whether a signal from the signal pill 200 is received (decision 604). That is, the first medication has been dissolved and provided to the patient and the time gap has elapsed. As a result of the signal from the signal pill 200 not being received (decision 604, "NO" branch), the IoT medicine container 140 maintains a lock of the IoT medicine container 140 (step 606). For example, the IoT medicine container 140 may include an overall lock such that the patient may not access any of the medications stored therein. In another example, the IoT medicine container 140 may include a plurality of sections where each section has a respective locking component. With no signal, any of the locking components may be maintained. For example, by maintaining the lock, the patient may not inadvertently ingest a second medication or pill too early that may result in a drug interaction.

As a result of the signal from the signal pill 200 being received (decision 604, "YES" branch), the IoT medicine container 140 generates and transmits an alert to the patient to take a further medication (step 608). With the first medication being taken and the time gap elapsing, a second medication that may have a drug interaction with the first medication may be taken without concern for the drug interaction. The IoT medicine container 140 may include an alarm component that is triggered to provide a sensory alarm to the patient (e.g., visual, auditory, haptic, etc.). In addition, the IoT medicine container 140 unlocks the IoT medicine container 140 (step 610). For example, the overall lock of the IoT medicine container 140 may be opened for the patient to access the medications stored therein. In another example, based on scheduling of when medications are to be taken, a specific section of the IoT medicine container 140 may be unlocked so that the patient is only provided access to the specific medication stored in the section.

Within a predetermined time from the alert being provided, the IoT medicine container 140 determines whether the second medication has been taken from the IoT medicine container 140 (decision 612). As a result of the medication not being taken out of the IoT medicine container 140 (decision 612, "NO" branch), the IoT medicine container 140 may continue to provide the alert so that the patient takes the second medication (e.g., to maintain a schedule of taking the medications). As a result of the signal from the IoT medicine container 140 being received (decision 612, "YES" branch), the IoT medicine container 140 may determine that the patient has likely taken the second medication. The IoT medicine container 140 may re-lock the IoT medicine container 140 or the corresponding section thereof. When a section including the second medication was unlocked, the IoT medicine container 140 may not re-lock the section as no medication is being held.

The exemplary embodiments may be provided that incorporates a variety of considerations and may also be performed with various modifications. For example, the medications that are prescribed to the patient may be based on patient specific characteristics (e.g., age, gender, co-morbidities, vitals, etc.). The medications that are prescribed may be indicated with the appropriate name, quantity, sequence, time gap, tec. In this manner, the exemplary embodiments may provide an appropriate instruction in generating the multi-medication pill 200 or the signal pill 300 using, for example, a three-dimensional medicine printing system to print a capsule or pill that allows for the time gap to be observed between medications.

The exemplary embodiments are configured to provide a plurality of medications with a time gap established therebetween to prevent a drug interaction between the medications. The exemplary embodiments may provide instructions to three-dimensionally print the pill as either a multi-medication pill or a signal pill based on whether a size of the resulting pill is acceptable for the patient (e.g., based on age, health condition, etc.). In the multi-medication pill, a first medication may be included in an outer medication portion and a second medication may be included in an inner medication portion. A filler may be used to separate the outer and inner medication portions. The filler may be selected to have a size (e.g., volume, thickness, etc.) such that the time gap is required to elapse between the medications. In the signal pill, a first medication may be included in an outer medication portion and an EEC may be included in an inner EEC portion. A filler may be used to separate the outer medication portion and the inner EEC portion. The filler may be selected to have a size such that the time gap is required to elapse before a signal is transmitted by the EEC. The signal may trigger an alert which is received by the patient to take a second medication.

Figure 7:
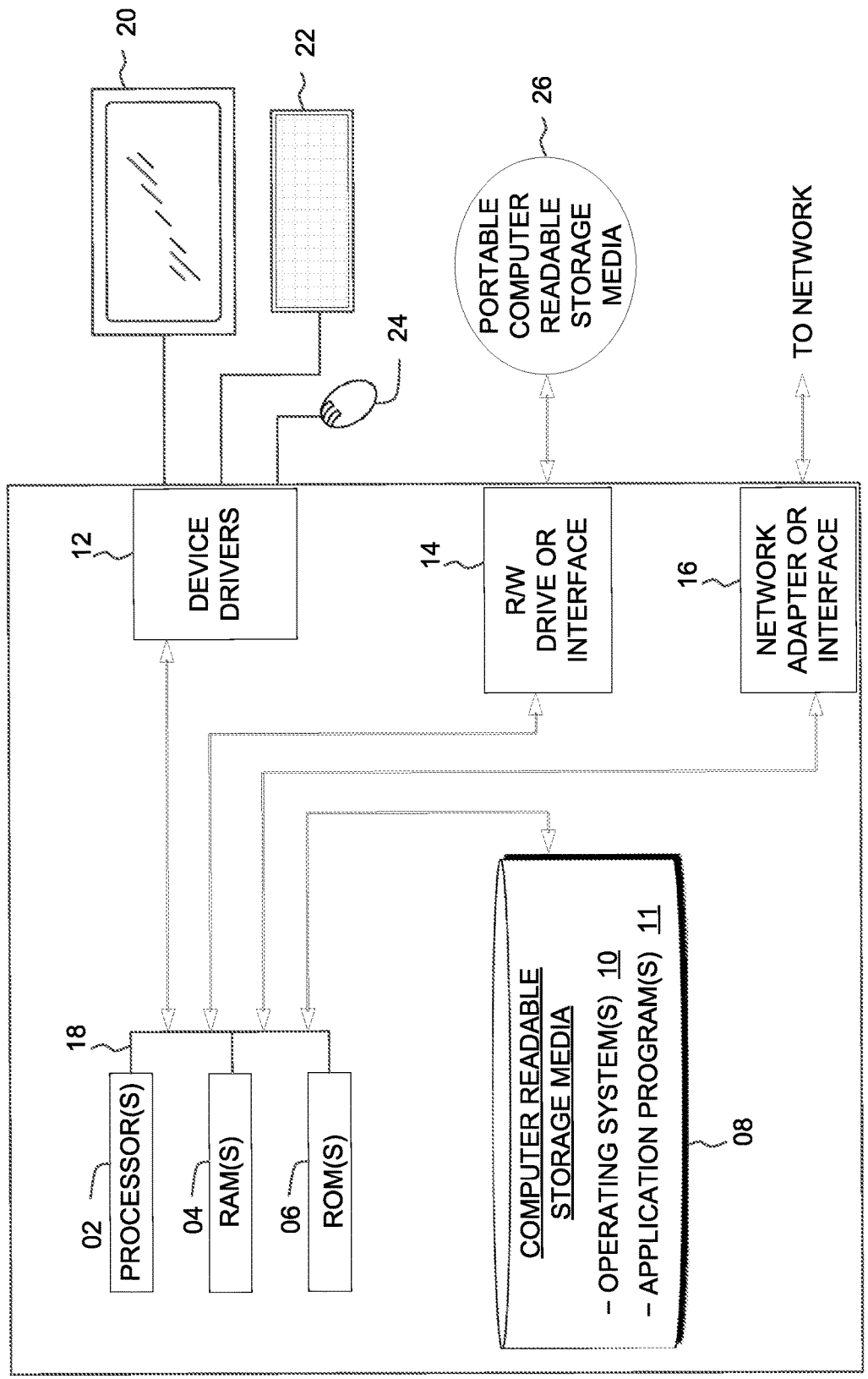
FIG. 7 depicts an exemplary block diagram depicting the hardware components of the medication system 100 of FIG. 1, in accordance with the exemplary embodiments.

FIG. 7 depicts a block diagram of devices within the medication system 100 of FIG. 1, in accordance with the exemplary embodiments. It should be appreciated that FIG. 7 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a RAY drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, RAY drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage sources, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
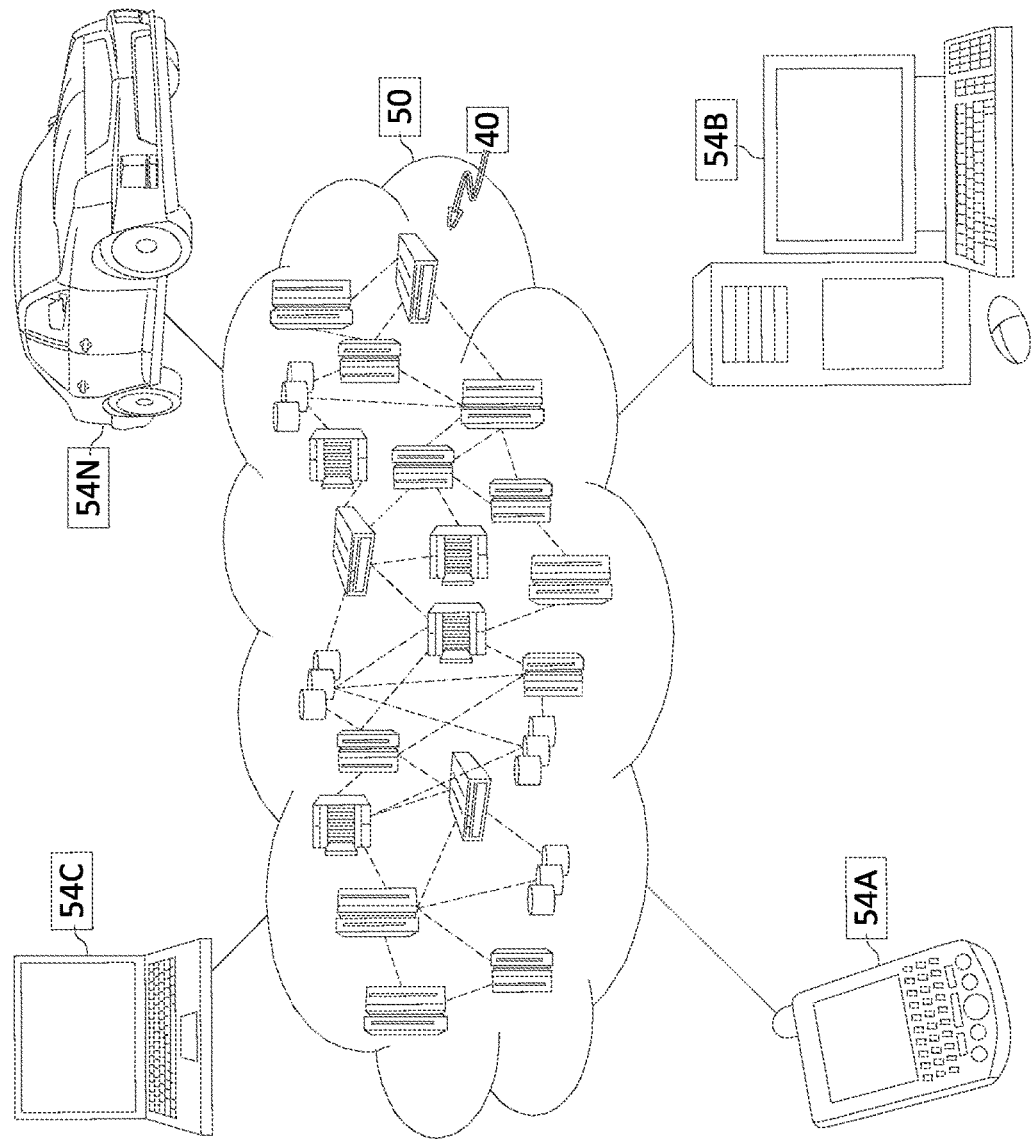
FIG. 8 depicts a cloud computing environment, in accordance with the exemplary embodiments.

Referring now to FIG. 8, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 40 and cloud computing environment 50 can communicate with any type of computerized device over any type of network and/or network addressable connection (e.g., using a web browser).

Figure 9:
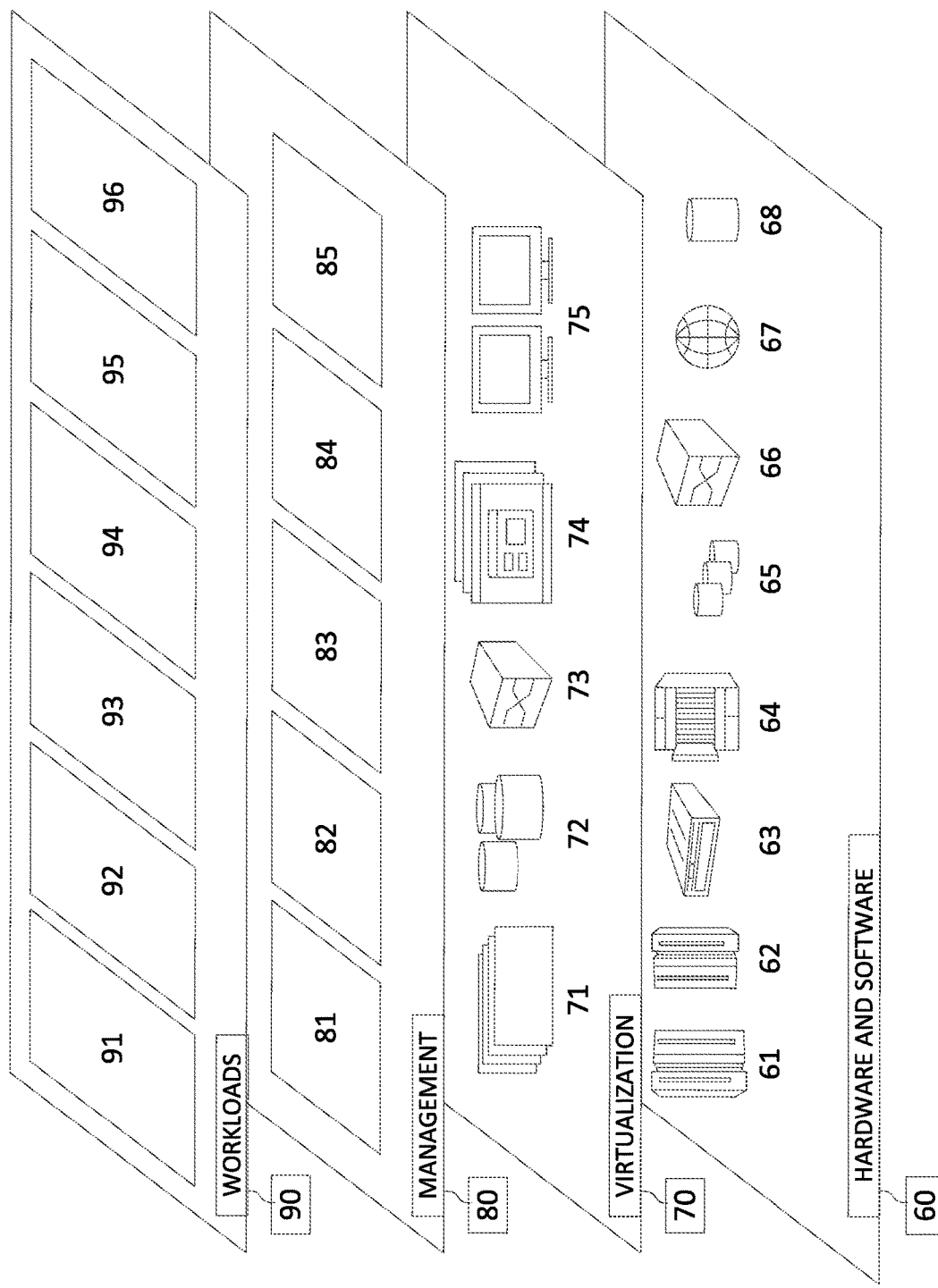
FIG. 9 depicts abstraction model layers, in accordance with the exemplary embodiments.

Referring now to FIG. 9, a set of functional abstraction layers provided by cloud computing environment 50 (FIG. 8) is shown. It should be understood in advance that the components, layers, and functions shown in FIG. 9 are intended to be illustrative only and the exemplary embodiments are not limited thereto. As depicted, the following layers and corresponding functions are provided:

Hardware and software layer 60 include hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and dissolving pattern processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for providing medications to a patient with a time gap, the method comprising:
   determining a dissolving pattern for the patient, the dissolving pattern including a medication dissolving rate for a first medication and a second medication prescribed to the patient and a filler dissolving rate for a filler selected so that the time gap is elapsed prior to the second medication being taken after the first medication, the medication dissolving rate and the filler dissolving rate being specific to the patient;
   determining dimensions of the first medication and the second medication to correspond to a dosage of the prescribed first medication and the prescribed second medication, respectively, and dimensions of the filler to accomplish the time gap; and
   based on determining a combination of the dimensions of the first medication, the second medication, and the filler contained in a multi-medication pill exceed a maximum pill size threshold for the patient, 3D printing a signal pill including at least the first medication, the filler, and an edible electronic circuit (EEC), the filler surrounding the EEC and the first medication surrounding the filler such that the first medication is dissolved prior to the filler being dissolved, the first medication and the filler 3D printed in accordance with the determined dimensions.

2. The computer-implemented method of claim 1, wherein the pill is a multi-medication pill, the multi-medication pill including the second medication, the second medication being surrounded by the filler.

3. The computer-implemented method of claim 1, wherein, after the filler has been dissolved to expose the EEC, the EEC is powered to transmit a signal, the signal configured to provide an alert to the patient that the time gap has elapsed.

4. The computer-implemented method of claim 3, wherein the EEC is piezoelectric such that exposure to stomach acid from the patient powers the EEC.

5. The computer-implemented method of claim 1, wherein determining the dissolving pattern is performed during a trial run, the trial run including providing a first monitoring pill including the first medication and a medication monitoring embedded circuit, an exposure of the medication monitoring embedded circuit generating a signal that is transmitted to define a medication time duration for the patient to dissolve the first medication, the trial run including providing a second monitoring pill including the filler and a filler monitoring embedded circuit, a further exposure of the filler monitoring embedded circuit generating a further signal that is transmitted to define a filler time duration for the patient to dissolve the filler.

6. The computer-implemented method of claim 1, wherein the time gap prevents a drug interaction between the first medication and the second medication.

7. A computer program product for providing medications to a patient with a time gap, the computer program product comprising:
one or more non-transitory computer-readable storage media and program instructions stored on the one or more non-transitory computer-readable storage media capable of performing a method, the method comprising:
determining a dissolving pattern for the patient, the dissolving pattern including a medication dissolving rate for a first medication and a second medication prescribed to the patient and a filler dissolving rate for a filler selected so that the time gap is elapsed prior to the second medication being taken after the first medication, the medication dissolving rate and the filler dissolving rate being specific to the patient;
determining dimensions of the first medication and the second medication to correspond to a dosage of the prescribed first medication and the prescribed second medication, respectively, and dimensions of the filler to accomplish the time gap; and
based on determining a combination of the dimensions of the first medication, the second medication, and the filler contained in a multi-medication pill exceed a maximum pill size threshold for the patient, 3D printing a signal pill including at least the first medication, the filler, and an edible electronic circuit (EEC), the filler surrounding the EEC and the first medication surrounding the filler such that the first medication is dissolved prior to the filler being dissolved, the first medication and the filler 3D printed in accordance with the determined dimensions.

8. The computer program product of claim 7, wherein the pill is a multi-medication pill, the multi-medication pill including the second medication, the second medication being surrounded by the filler.

9. The computer program product of claim 7, wherein, after the filler has been dissolved to expose the EEC, the EEC is powered to transmit a signal, the signal configured to provide an alert to the patient that the time gap has elapsed.

10. The computer program product of claim 9, wherein the EEC is piezoelectric such that exposure to stomach acid from the patient powers the EEC.

11. The computer program product of claim 7, wherein determining the dissolving pattern is performed during a trial run, the trial run including providing a first monitoring pill including the first medication and a medication monitoring embedded circuit, an exposure of the medication monitoring embedded circuit generating a signal that is transmitted to define a medication time duration for the patient to dissolve the first medication, the trial run including providing a second monitoring pill including the filler and a filler monitoring embedded circuit, a further exposure of the filler monitoring embedded circuit generating a further signal that is transmitted to define a filler time duration for the patient to dissolve the filler.

12. The computer program product of claim 7, wherein the time gap prevents a drug interaction between the first medication and the second medication.

13. A computer system for providing medications to a patient with a time gap, the computer system comprising:
one or more computer processors, one or more computer-readable storage media, and program instructions stored on the one or more of the computer-readable storage media for execution by at least one of the one or more processors capable of performing a method, the method comprising:
determining a dissolving pattern for the patient, the dissolving pattern including a medication dissolving rate for a first medication and a second medication prescribed to the patient and a filler dissolving rate for a filler selected so that the time gap is elapsed prior to the second medication being taken after the first medication, the medication dissolving rate and the filler dissolving rate being specific to the patient;
determining dimensions of the first medication and the second medication to correspond to a dosage of the prescribed first medication and the prescribed second medication, respectively, and dimensions of the filler to accomplish the time gap; and
based on determining a combination of the dimensions of the first medication, the second medication, and the filler contained in a multi-medication pill exceed a maximum pill size threshold for the patient, 3D printing a signal pill including at least the first medication, the filler, and an edible electronic circuit (EEC), the filler surrounding the EEC and the first medication surrounding the filler such that the first medication is dissolved prior to the filler being dissolved, the first medication and the filler 3D printed in accordance with the determined dimensions.

14. The computer system of claim 13, wherein the pill is a multi-medication pill, the multi-medication pill including the second medication, the second medication being surrounded by the filler.

15. The computer system of claim 13, wherein, after the filler has been dissolved to expose the EEC, the EEC is powered to transmit a signal, the signal configured to provide an alert to the patient that the time gap has elapsed.

16. The computer system of claim 15, wherein the EEC is piezoelectric such that exposure to stomach acid from the patient powers the EEC.

17. The computer system of claim 13, wherein determining the dissolving pattern is performed during a trial run, the trial run including providing a first monitoring pill including the first medication and a medication monitoring embedded circuit, an exposure of the medication monitoring embedded circuit generating a signal that is transmitted to define a medication time duration for the patient to dissolve the first medication, the trial run including providing a second monitoring pill including the filler and a filler monitoring embedded circuit, a further exposure of the filler monitoring embedded circuit generating a further signal that is transmitted to define a filler time duration for the patient to dissolve the filler.

\* \* \* \* \*